US007777000B2

(12) United States Patent
Gallo et al.

(10) Patent No.: US 7,777,000 B2
(45) Date of Patent: Aug. 17, 2010

(54) ANTI-VIRAL ACTIVITY OF CATHELICIDIN PEPTIDES

(75) Inventors: Richard L. Gallo, San Diego, CA (US); Donald Y. M. Leung, Denver, CO (US); James F. Jones, Decatur, GA (US)

(73) Assignee: The Regents of the University of California, Oakland, CA (US)

( * ) Notice: Subject to any disclaimer, the term of this patent is extended or adjusted under 35 U.S.C. 154(b) by 752 days.

(21) Appl. No.: 10/546,739

(22) PCT Filed: Mar. 5, 2004

(86) PCT No.: PCT/US2004/006952
§ 371 (c)(1),
(2), (4) Date: Jul. 31, 2006

(87) PCT Pub. No.: WO2004/098536
PCT Pub. Date: Nov. 18, 2004

(65) Prior Publication Data
US 2006/0292551 A1 Dec. 28, 2006

Related U.S. Application Data

(60) Provisional application No. 60/452,906, filed on Mar. 6, 2003.

(51) Int. Cl.
*C07K 14/00* (2006.01)
*A61K 38/17* (2006.01)
(52) U.S. Cl. ..................... 530/324; 424/93.1
(58) Field of Classification Search ........................ None
See application file for complete search history.

(56) References Cited

U.S. PATENT DOCUMENTS

| 4,482,680 | A | 11/1984 | Sheldon |
| 5,618,675 | A | 4/1997 | Larrick et al. |
| 5,786,328 | A | 7/1998 | Dennis et al. |
| 6,020,121 | A | 2/2000 | Bao et al. |
| 6,040,291 | A | 3/2000 | Hirata |
| 7,173,007 | B1 | 2/2007 | Zaiou |
| 7,452,864 | B2 | 11/2008 | Stahle-Backdahl et al. |
| 2003/0022829 | A1* | 1/2003 | Maury et al. ............... 514/12 |
| 2004/0087559 | A1 | 5/2004 | Schwartz et al. |
| 2006/0115480 | A1 | 6/2006 | Hillman |
| 2006/0292551 | A1 | 12/2006 | Gallo et al. |
| 2007/0037744 | A1 | 2/2007 | Gallo |
| 2007/0065908 | A1 | 3/2007 | Gallo |
| 2009/0318534 | A1 | 12/2009 | Gallo et al. |

FOREIGN PATENT DOCUMENTS

| EP | 1 358 888 A1 | 11/2003 |
| WO | 96/08508 | 3/1996 |
| WO | WO99/09322 A2 * | 2/1999 |
| WO | 02/13857 | 2/2002 |
| WO | WO 02/13857 A2 | 2/2002 |
| WO | 02/060468 | 8/2002 |
| WO | 02/60468 A2 | 8/2002 |
| WO | WO 02/060468 A2 | 8/2002 |
| WO | 03047594 A1 | 6/2003 |
| WO | 2004/098536 | 11/2004 |
| WO | 2005/040192 | 5/2005 |
| WO | 2005/040201 | 5/2005 |

OTHER PUBLICATIONS

Popsueva et al. FEBS Letter 1996, vol. 391, pp. 5-8.*
Steinstraesser et al. Retrovitrovirology 2005, vol. 2.2 pp. 1-12.*
Yedery et al. The European Journal of Contraception and Reproduction Health Care, 2005, vol. 10, No. 1, pp. 32-42.*
Gordon et al. Current Eye Research 2005, vol. 30, pp. 385-394.*
Benincasa, Monica et al., "In vitro and in vivo antimicrobial activity of two alpha-helical cathelicidin peptides and of their synthetic analogs," Peptides, vol. 24, No. 11, pp. 1723-1731, Nov. 2003.
Bowman, et al. "Prepro-FALL-99" Jun. 6, 1996, Database: A.sub.—Geneseq.sub.—21, Accession No. AAR92924, alignment result 4.
Brasei, Kenneth et al., Hematologic Effects on flt3 Ligand in Vivo in Mice, Blood, vol. 88, No. 6, pp. 2004-2012, 1996.
Clinical and Experimental Dermatology vol. 21, No. 3, pp. 185, May 1996.
Gallo, Richard L. et al., "Identification of CRAMP, a cathelin-related antimicriobial peptide expressed in the embryonic and adult mouse," J. Biol. Chem., vol. 272, No. 20, pp. 13088-13093, May 16, 1997.
Gennaro, Renato et al., "Pro-rich antimicrobial peptides from animals: structure, biological functions and mechanism of action," Current Pharmaceutical Design. vol. 8, No. 9, pp. 763-778, 2002.
Gennaro, Renato et al., "Structural features and biological activities of the cathelicidin-derived antimicrobial peptides," Biopolymers, vol. 55, No. 1, pp. 31-49, 2000.
Gennaro, Renato et al., "Biological characterization of a novel mammalian antimicrobial peptide," Biochimica et Biophysica Acta, vol. 1425, No. 2, pp. 361-368, Oct. 23, 1998.
Ha, Jong-Myung et al., "Synthesis and Antibiotic Activities of CRAMP, a Cathelin-related Antimicrobial Peptide and Its Fragments," Bull. Korean Chem. Soc., vol. 20, No. 9, pp. 1073-1077, 1999.
Howell, Michael D. et al., "Selective Killing of Vaccinia Virus by LL-37: Implications for Eczema Vaccinatum," Journal of Immunology, vol. 172, pp. 1763-1767, 2004.
Johansson, J.; G. H. Gudmundsson; M. E. Rottenberg; K. D. Berndt; and B. Agerberth; "Conformation-dependent Antibacterial Activity of the Naturally Occurring Human Peptide LL-37" The Journal of Biological Chemistry; Feb. 6, 1998; 273(6):3718-3724.
Johnson, B. Connor, "Posttranslational Covalent Modification of Proteins," Academic Press, NY, pp. 1-12 1983.

(Continued)

*Primary Examiner*—Nolan Patrick
*Assistant Examiner*—Bao Qun Li
(74) *Attorney, Agent, or Firm*—Joseph R. Baker, Jr.; Gavrilovich Dodd & Lindsey LLP

(57) ABSTRACT

The disclosure provides methods and compositions useful in the treatment of dermatitis and viral infections. The compositions comprise cationic peptides of the cathelicidin family including LL-37, related homologues, and variants thereof.

9 Claims, 7 Drawing Sheets

OTHER PUBLICATIONS

Kaufman, Randal et al., "Synthesis, Processing, and Secretion of Recombinant Human Factor VIII Expressed in Mammalian Cells," Journal of Biological Chemistry vol. 263, No. 13, pp. 6352-6362, 1988.

Kaufman, Randal, "Selection and Coamplification of Heterologous Genes in Mammalian Cells" Methods in Enzymology, vol. 185 pp. 527-566, 1990.

McKinnon, P et al., "Expression, purification and characterization of secreted recombinant human insulin-like growth factor—I (IGF-I) and the potent variant des(1-3) IGF-I in Chinese hamster ovary cells" Journal Molecular Endocrinology 6, pp. 231-239, 1991.

Merrifield, R.B.. "Solid Phase Peptide Synthesis" Journal. Am. Chem. Soc., vol. 85, pp. 2149, 1962.

Ong, Peck et al., "Endogenous Antimicrobial Peptides and Skin Infections in Atopic Dermatitis," New England Journal of Medicine, vol. 347, No. 15, pp. 1151-1160, Oct. 10, 2002.

Rattan, Suresh I. et al., "Protein Synthesis, Posttranslational Modifications, and Aging," Annals of the N. Y. Academy of Science, vol. 663, pp. 48-62 (1992).

Sanchez et al., "Overexpression and structural study of the cathelicidin motif of the protegrin-3 precursor," Biochemistry, vol. 41, No. 1, pp. 21-30, Jan. 8, 2002.

Scott, Jamie et al.,"Searching for Peptide Ligands with an Epitope Library," Science Voll. 249, pp. 386-390 (1990).

Seifter, Sam et al., "Analysis for Protein Modifications and Nonprotein Cofactors," Methods of Enzymology, vol. 182, pp. 626-646,1990.

Skerlavaj, Barbara et al., "Structural and functional analysis of horse cathelicidin peptides," Antimicrobial Agents Chemotherapy., vol. 45, No. 3, pp. 715-722, Mar. 2001.

Smeianov, Vladimir et al. "Activity of cecropin P1 and FA-LL-37 Against urogenital microflora" Microbes and Infection, vol. 2, pp. 773-777, 2000.

Smith, George, et al., "Libraries of Peptides and Proteins Displayed on Filamentous Phage," Methods Enzymology, vol. 217, pp. 228-257, 1993.

Stewart, John, et al., "Solid Phase Peptides Synthesis," W.H. Freeman and Company, San Francisco, 1969, pp. 27-62.

Tjabringa, G. Sandra et al., "The Antimicrobial Peptide LL-37 Activates Innate Immunity at the Airway Epithelial Surface by Transactivation of the Epidermal Growth Factor Receptor," Journal of Immunology, vol. 171, pp. 6690-6696, 2003.

Urlaub, Gail et al., "Isolation of Chinese Hamster cell mutants deficient in dihydrofolate reductase activity," Proc Natl Acad Sci USA, vol. 77, pp. 4216-4220, 1980.

Wood, Clive et al.,"High Level Synthesis Of Immunoglobulins In Chinese Hamster Ovary Cells," The Journal of Immunology, Vo. 145, pp. 3011-3016, 1990.

Zaiou, Mohamed et al., "Antimicrobial and Protease Inhibitory Functions of the Human Cathelicidin (hCAP18/LL-37) Prosequence," The Society for Investigative Dermatology, vol. 120, No. 5, pp. 810-816, May 2003.

Zanetti, Margherita et al., "Cathelicidin peptides as candidates for a novel class of antimicrobials," Current Pharmaceutical Design, vol. 8, No. 9, pp. 779-793, 2002.

Zanetti, Margherita et al., "Structure and biology of cathelicidins," Adv. Exp. Med. Biol., vol. 479, pp. 203-218, 2000.

Zanetti, Margherita et al., "The cathelicidin family of antimicrobial peptide precursors: a component of the oxygen-independent defense mechanisms of neutrophils," Annals N. Y. Academy of Scieces, vol. 832, pp. 147-162, Dec. 15, 1997.

Zanetti, Margherita et al. "Cathelicidin Peptides as Candidates for a Novel Class of Antimicrobials" Current Pharmaceutical Design, vol. 8, No. 9, pp. 779-793, 2002.

Braun, et al. "Setting the stage for bench-to-bedside movement of anti-HIV RNA inhibitors-gene therapy for AIDS in macaques." Frontiers in Bioscience, vol. 11, pp. 838-851, Jan. 2006.

CDC Fact Sheet: Genital HPV, pp. 1-2, Dec. 2007.

Cordero Garcia, Marcela M., International Search Report and Written Opinion, Date of Mailing of Report: Aug. 1, 2008, International Application No. PCT/US07/19485, 6 pages.

Cussac, Yolaine, International Preliminary Report on Patentability and Written Opinion, date of issuance of report: Mar. 31, 2009, International Application No. PCT/US2007/021029, 6 pages.

Field, et al. "Herpesvirus Latency and Therapy-From a veterinary perspective." Antiviral Research, vol. 71, pp. 127-133, 2007.

Gait, et al. "Progress in anti-HIV structure based drug design." TIBTECH, vol. 13, pp. 430-438, Oct. 1995.

Gill, et al. "The role of Toll-Like Receptor Ligands/Agonist in Protection Against Genital HSV-2 Infection." American Journal of Reproductive Immunology, vol. 59, pp. 35-43, 2008.

Goodyear, H.M., "Growth of herpes simplex type 1 on skin explants of atopic eczema." Clinical and Experimental Dermatology, May 1996, vol. 21, No. 3, pp. 185-189.

Kim, Jun Kyung, International Search Report and Written Opinion, Date of Mailing of Search Report: Oct. 27, 2008, International Application Number, 13 pages.

Kleymann, et al. "Agents and strategies in development of improved management of herpes simplex virus infection and disease." Expert Opin. Investig. Drugs, vol. 14(2), pp. 135-161, 2005.

Kreger, Arnold S. et al, "Purification and Properties of Stapylococcal Delta Hemolysin" Infection and Immunity, Mar. 1971, pp. 449-465, vol. 3, No. 3.

Kuwahara, Yoshiko, International Preliminary Report on Patentability and Written Opinion, date of issuance of report: Aug. 26, 2009, International Application No. PCT/US2008/054453, 7 pages.

Liles, W. Conrad et al, "Stimulation of Human Neutrophils and Monocytes by Stapylococcal Phenol-Soluble Modulin" Journal of Leukocyte Biology, Jul. 2001, pp. 96-102, vol. 70.

Lindner, Nora, International Preliminary Report on Patentability and Written Opinion, Date of Issuance of Report: Mar. 10, 2009, International Application No. PCT/US07/19485.

Mehlin, Christopher et al, "An Inflammatory Polypeptide Complex from Staphylococcus Epidermidis; Isolation and Characterization" Journal Exp. Med, Mar. 15, 1999, pp. 907-917, vol. 189, No. 6.

McGarry, Sean R., The International Search Report and Written Opinion, Date of Mailing of Report: Aug. 7, 2008, International Application No. PCT/US07/21029, May 25, 2010.

Schroder, J.M. et al, "Antimicrobial Skin Peptides and Proteins" CMLS Cellular and Molecular Life Sciences, Birkhauser-Verlag, BA, vol. 63 No. 4, Feb. 1, 2006, pp. 469-486, XP019201029.

Uryga-Polowy, V; Supplementary Partial European Search Report, date of completion of search: Sep. 4, 2009, Application No. EP07867175, 17 pages.

Wang, T-T et al; "Cutting Edge; 1, 25-Dihydroxyvitamin D3 Is a Direct Inducer of Antimicrobial Peptide Gene Expression" Journal of Immunology, American Association of Immunologists, US, vol. 73, Jan. 1, 2004, pp. 2909-2912, XP002992051.

Wheeler, Thomas T. et al. "The Mammalian Innate Immune System: Potential Targets for Drug Development." Current Drug Targets—Immune, Endocrine & Metabolic Disorders, 2005, vol. 5, pp. 237-247.

Yamasaki K; et al, "301—Expression and Potential Pathological Role of Cathelicidin Expression in Rosacea" Journal of Investigative Dermatology, vol. 122, No. 3, Mar. 2004, p. A51, XP009122113.

Yamasaki, Kenshi et al. "Kallikrein-mediated proteolysis regulates the antimicrobial effects of cathelicidins in skin." The FASEB Journal, 2006,vol. 20, pp. 2068-2080.

\* cited by examiner

A          B

```
CRAMP Mature Peptide:     GLLRKGGEKIGEKLKKIGQKIKNFFQKLVPQPEQ
LL-37 Mature Peptide:     LLGDFFRKSKEKIGKEFKRIVQRIKDFLRNLVPRTES
      Consensus    :         RK  EKIG   K I Q IK F   LVP  E
```

FIGURE 7

SEQUENCE LISTING

<160> NUMBER OF SEQ ID NOS: 12

<210> SEQ ID NO 1
<211> LENGTH: 37
<212> TYPE: PRT
<213> ORGANISM: Homo sapiens

<400> SEQUENCE: 1

Leu Leu Gly Asp Phe Phe Arg Lys Ser Lys Glu Lys Ile Gly Lys Glu
 1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 739
<212> TYPE: DNA
<213> ORGANISM: Homo sapiens

```
<400> SEQUENCE: 2
taaagcaaac cccagcccac accctggcag gcagccaggg atgggtggat caggaaggct     60
cctggttggg cttttgcatc aggctcaggc tgggcataaa ggaggctcct gtgggctaga    120
gggaggcaga catggggacc atgaagaccc aaagggatgg ccactccctg gggcggtggt    180
cactggtgct cctgctgctg ggcctggtga tgcctctggc catcattgcc caggtcctca    240
gctacaagga agctgtgctt cgtgctatag atggcatcaa ccagcggtcc tcggatgcta    300
acctctaccg cctcctggac ctggacccca ggcccacgat ggatggggac ccagacacgc    360
caaagcctgt gagcttcaca gtgaaggaga cagtgtgccc caggacgaca cagcagtcac    420
cagaggattg tgacttcaag aaggacgggc tggtgaagcg gtgtatgggg acagtgaccc    480
tcaaccaggc caggggctcc tttgacatca gttgtgataa ggataacaag agatttgccc    540
tgctgggtga tttcttccgg aaatctaaag agaagattgg caaagagttt aaaagaattg    600
tccagagaat caaggatttt tgcggaatc ttgtacccag acagagtcc tagtgtgtgc     660 cctaccctgg ctcaggcttc tgggctctga aaataaact atgagagcaa tttcaaaaaa    720
aaaaaaaaaa aaaaaaaaa                                                 739

<210> SEQ ID NO 3
<211> LENGTH: 34
<212> TYPE: PRT
<213> ORGANISM: Mus musculus

<400> SEQUENCE: 3

Gly Leu Leu Arg Lys Gly Gly Glu Lys Ile Gly Glu Lys Leu Lys Lys
 1               5                  10                  15

Ile Gly Gln Lys Ile Lys Asn Phe Phe Gln Lys Leu Val Pro Gln Pro
            20                  25                  30

Glu Gln

<210> SEQ ID NO 4
<211> LENGTH: 592
<212> TYPE: DNA
<213> ORGANISM: Mus musculus

<400> SEQUENCE: 4
tcagtcttgg gaaccatgca gttccagagg acgtcccct ccctgtggct gtggcggtca      60
ctatcactgc tgctgctact gggcctgggg ttctcccaga ccccagcta cagggatgct    120 gtgctccgag ctgtggatga cttcaaccag cagtccctag acaccaatct ctaccgtctc    180
ctggacctgg atcctgagcc caaggggac gaggatccag atactcccaa gtctgtgagg     240
ttccgagtga aggagactgt atgtggcaag gcagagcggc agctacctga gcaatgtgcc    300
ttcaaggaac aggggtggt gaagcagtgt atggggcag tcaccctgaa cccggccgct      360
gattcttttg acatcagctg taacgagcct ggtgcacagc cctttcggtt caagaaaatt    420
tcccggctgg ctggacttct ccgcaaaggt ggggagaaga ttggtgaaaa gcttaagaaa    480
attggcagaa aaattaagaa ttttttcag aaacttgtcc ctcagccaga gtagtaggcc     540
tgccttggcc tgtttctgga ttccctaaaa ttataaactt ggtaaaaaaa aa            592

<210> SEQ ID NO 5
<211> LENGTH: 5
<212> TYPE: PRT
<213> ORGANISM: Artificial Sequence
<220> FEATURE:
<223> OTHER INFORMATION: synthetically generated peptide
```

```
<400> SEQUENCE: 5

Gly Gly Gly Gly Ser
1               5

<210> SEQ ID NO 6
<211> LENGTH: 22
<212> TYPE: PRT
<213> ORGANISM: Artificial Sequence
<220> FEATURE:
<223> OTHER INFORMATION: synthetically generated peptide

<400> SEQUENCE: 6

Gly Gly Gly Gly Gly Gly Ser Met Phe Gly Gly Ala Lys Lys Arg Ser
1               5                  10                  15

Gly Gly Gly Gly Gly Gly
            20

<210> SEQ ID NO 7
<211> LENGTH: 20
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 11
<223> OTHER INFORMATION: Xaa = selenocysteine (U)

<400> SEQUENCE: 7

Gly Leu Asn Gly Pro Asp Ile Tyr Lys Gly Xaa Tyr Gln Phe Lys Ser
1               5                  10                  15

Val Glu Phe Asp
            20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gccaatgagg gttcgagttc                                           20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
caacatcccg tcgttcatca                                           20

<210> SEQ ID NO 10
<211> LENGTH: 34
<212> TYPE: PRT
<213> ORGANISM: Homo sapiens

<400> SEQUENCE: 10

Gly Leu Leu Arg Lys Gly Gly Glu Lys Ile Gly Glu Lys Leu Lys Lys
1               5                  10                  15

Ile Gly Gln Lys Ile Lys Asn Phe Phe Gln Lys Leu Val Pro Gln Pro
            20                  25                  30
```

```
-continued

Glu Gln

<210> SEQ ID NO 11
<211> LENGTH: 37
<212> TYPE: PRT
<213> ORGANISM: Mus musculus

<400> SEQUENCE: 11

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 12
<211> LENGTH: 30
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(30)
<223> OTHER INFORMATION: Xaa = any amino acid

<400> SEQUENCE: 12

Arg Lys Xaa Xaa Glu Lys Ile Gly Xaa Xaa Xaa Lys Xaa Ile Xaa Gln
1               5                   10                  15

Xaa Ile Lys Xaa Phe Xaa Xaa Xaa Leu Val Pro Xaa Xaa Glu
            20                  25                  30
```

ANTI-VIRAL ACTIVITY OF CATHELICIDIN PEPTIDES

CROSS REFERENCE TO RELATED APPLICATIONS

This application is filed under 35 U.S.C. §371 and claims priority to International Application Serial No. PCT/US2004/006952, filed Mar. 5, 2004, which claims priority under 35 U.S.C. §119 from provisional application Ser. No. 60/452,906, filed Mar. 6, 2003, the disclosure of which is incorporated herein by reference.

STATEMENT AS TO FEDERALLY SPONSORED RESEARCH

The U.S. Government has certain rights in this disclosure pursuant to Grant Nos. AR41256 and AI052453 awarded by the National Institutes of Health.

TECHNICAL FIELD

The disclosure relates peptides that have antiviral activity.

BACKGROUND

Virus infections occur following entrance of virions into host cells by a variety of mechanisms including endocytosis of non-enveloped viruses and fusion with the cell membrane by enveloped viruses. One primary barrier to the infection is epithelial keratinocyte of the skin. Alterations in skin barrier function are seen in atopic dermatitis (AD). This finding may contribute to infection with bacteria and selected viruses, including Herpesviridae (herpes simplex virus (HSV), *varicella*-zoster virus) and vaccinia virus. However, it is unlikely that a defect in the physical barrier alone accounts for the remarkably increased susceptibility of AD patients to recurrent skin infections. Patients with plaque psoriasis, a common Th1-mediated inflammatory skin disease also associated with skin barrier dysfunction, do not have increased susceptibility to microbial skin infection.

SUMMARY

The disclosure provides a purified cationic antiviral peptide comprising antiviral activity and a sequence as set forth in SEQ ID NO:1 or a variant thereof, or as set forth in SEQ ID NO:3 or a variant thereof.

Also provided by the disclosure is an isolated polynucleotide that encodes a cationic antiviral peptide of SEQ ID NO:1 or a variant thereof, or of SEQ ID NO:3 or a variant thereof. In one aspect, the polynucleotide is selected from the group consisting of (i) a polynucleotide encoding a cationic antiviral peptide or variant; (ii) a polynucleotide encoding SEQ ID NO:1 or a variant thereof; (iii) a polynucleotide encoding SEQ ID NO:3 or variant thereof; (iv) a polynucleotide comprising SEQ ID NO:2; (v) a polynucleotide comprising SEQ ID NO:4; (vi) a polynucleotide comprising SEQ ID NO:2, wherein T is U; (vii) a polynucleotide comprising SEQ ID NO:4, wherein T is U; and (v) a polynucleotide comprising a sequence that is complementary to (iv), (v), (vi), or (vii).

The disclosure also provides a method for inhibiting the spread and/or reducing the risk of infection of a virus comprising contacting a virus with an inhibiting effective amount of a cationic antiviral peptide composition. In one aspect, the cationic antiviral peptide composition comprises a cationic antiviral peptide having the sequence as set forth in SEQ ID NO:1. In another aspect, the cationic antiviral peptide composition comprises a cationic antiviral peptide having the sequence as set forth in SEQ ID NO:3. In yet another aspect, the cationic antiviral peptide composition comprises a cationic LL-37 peptide and a cationic CRAMP peptide.

The disclosure further provides a method of treating atopic dermatitis comprising contacting a subject having or suspected of having atopic dermatitis with an inhibiting effective amount of a cationic antiviral peptide composition.

The disclosure provides a method of determining the presence of, or predisposition of, a subject to dermatitis comprising measuring LL-37 in the skin of a subject.

The disclosure also provides a method of diagnosing atopic dermatitis in a subject comprising quantifying polynucleotides encoding LL-37 in cells isolated from the subject, wherein the amount of LL-37 is indicative of atopic dermatitis.

The disclosure provides a method of treating a dermatitis in a subject comprising administering a cationic LL-37 peptide or variant thereof, and/or a cationic CRAMP peptide or variant thereof to the subject.

The disclosure further provides a pharmaceutical composition comprising a cationic LL-37 peptide and/or a cationic CRAMP peptide and a pharmaceutically acceptable carrier. In one aspect, the pharmaceutical composition is designed for topical delivery to a subject.

The disclosure also provides a method for inhibiting an atopic dermatitis associated disorder in a subject having or at risk of having such the disorder, comprising administering to the subject a therapeutically effective amount of a cationic antiviral peptide composition.

The disclosure further provides a knock out non-human transgenic animal that lacks expression of a cathelicidin or homologue thereof and having increased susceptibility to viral infections of the skin.

The disclosure provides a method for screening an agent comprising administering the agent to a knockout non-human animal that lacks expression of a cathelicidin or homologue thereof and having increased susceptibility to viral infections of the skin, and measuring a dermatitis reaction in the knockout animal.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 7 shows a pile up showing the conservation of certain amino acids between a cationic LL-37 peptide (SEQ ID NO: 1) and a cationic CRAMP peptide (SEQ ID NO: 2). Accordingly, one of skill in the art can identify residues that can be conservatively substituted based upon the alignment.

DETAILED DESCRIPTION

Figure 1:
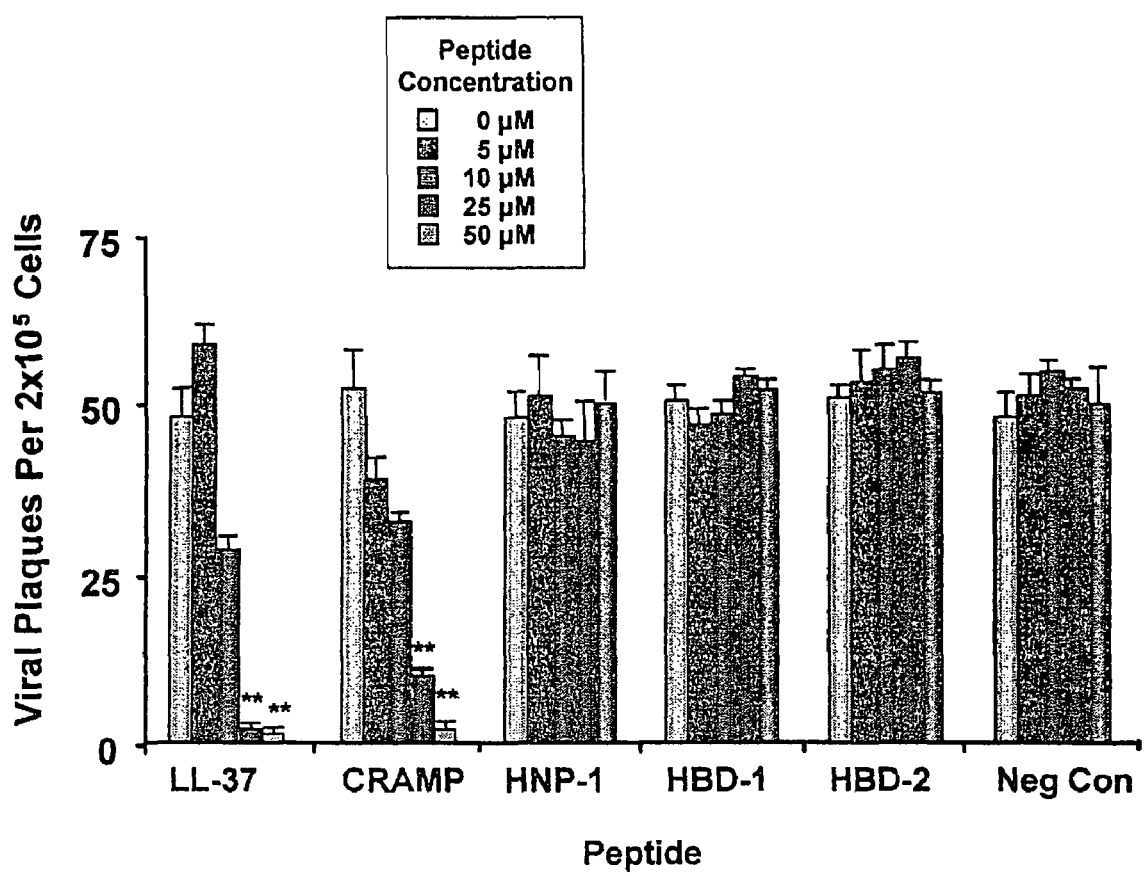
FIG. 1 shows plaque-forming units of vaccinia virus following incubation with antimicrobial and control peptides. P values are comparing vaccinia alone to reduction in virus at varying concentrations of the individual peptides. **P values for LL-37 respectively at 10, 25 and 50 µM: p=0.0041; p=<0.0001; and p=<0.0001. For CRAMP, they were respectively at 10, 25, and 50 µM: p=0.0113; p=0.0002; and p=<0.0001. These data are representative of six experiments with four replicates per condition.

The disclosure provides peptides useful in treating dermatitis and viral infections. As long as there is an apparent need for protection against smallpox and related viruses the evaluation of host responses that contribute to control of virus infections in general is an important goal.

Although the live virus smallpox vaccine has been shown to be highly effective, it has the dubious distinction of having one of the highest rates of vaccine-associated adverse events. Many of these adverse events may relate to a failure of the host to control vaccinia virus replication and dissemination. Furthermore, there is no effective antiviral agent that can be used therapeutically against vaccinia infection.

The disclosure demonstrates human and murine cathelicidins have innate antiviral activity and are capable of interfering in vitro and in vivo with replication of vaccinia virus. LL-37 and CRAMP were effective at concentrations at least one log lower than required for killing of S. aureus. The cationic peptides α-defensin HNP-1, and the β-defensins, HBD-1 and HBD-2, did not inhibit viral replication.

These unexpected results show that not all cationic and membrane active peptides have antiviral activity since LL37 and CRAMP, but not HBD-2, was able to inhibit viral vaccinia replication. The relative specificity demonstrates that specific structural elements of the cathelicidins are required for the observed effects. The mechanisms by which cationic human antimicrobial peptides kill bacteria and fungi are generally through binding of the peptide to the microbial cell membrane, after which the membrane's proton gradient and integrity are lost.

Intracellular mature virions (IMV) of vaccinia have a double layer membrane of endoplasmic reticulum derived membrane cisternae. As the IMV migrates through an infected cell the virion acquires a double layer outer envelope consisting of a cellular cisternae known as a wrapping membrane and become intracellular enveloped virions. Egress from the cell is accompanied by fusion of the outermost layer with the plasma membrane yielding a three layer outer membrane on extra-cellular enveloped virions (EEV). Both the IMV and EEV forms are infectious with the EEV being most efficient in cell entry. The disclosure demonstrates that cationic LL-37 peptides, related homologues, and variants thereof, are effective at disrupting the IMV and EEV of the virions thus being useful as antiviral agents.

The disclosure is the use of cathelicidins for treatment of viral skin disease, especially the use of LL-37 and CRAMP for the treatment of vaccinia and small pox infection. As the molecules are proteins, they are most well suited for topical application. However, peptidomimetics and other protein analogs with more favorable pharmacokinetic and pharmacodynamic properties can be developed for use with other routes of administration including, but not limited to, oral and parenteral. The compounds can be incorporated into appropriate delivery devices dependent upon the route of administration and other considerations well known to those skilled in the art. Peptides and peptidomimetics can be based on the functional domain of the cathelicidin or the entire length of the cathelicidin. Additionally as cathelicidins are peptides, the coding sequence could be delivered to the site of interest using any gene transfer protocol to allow for expression of the gene product.

The cathelicidins can be used in conjunction with vaccination to ameliorate or prevent eczema vaccination or after vaccination for the treatment of skin conditions. The cathelicidins can also be used for infections developed due to infection from other sources.

The disclosure is the use of the determination of LL-37 deficiency to exclude individuals from voluntary or prophylactic small pox vaccination. Skin biopsies, keratinocytes obtained by tape stripping or blood tests can be used to detect deficiencies in LL-37, wherein a deficiency indicates a risk of adverse effects associated with vaccination.

The disclosure provides a cationic peptide, LL-37, which has antiviral activity. The peptide is useful for inhibiting viral infection or spread, as well reducing the effects of viral infection. The peptide can be used, for example, as an antiviral agent in topical lotions as well as in other pharmaceuticals including soaps and wipes. The peptide of the disclosure can be used alone or in combination with conventional antiviral agents and can be used as an adjunct therapy.

Resolution of infection and protection against re-infection with viruses depends on cooperation between innate and adaptive immune processes. These processes include antiviral proteins, complement activation, macrophages, NK, numerous cytokines, cytotoxic T cells, specific antibodies and γ/δT cells. In addition to the alteration in the skin barrier in atopic dermatitis (AD), alterations in cellular immunity have been described in this disease. These alterations are possible candidate mechanisms for the serious consequences of herpes viruses and vaccinia virus in this skin disease. Goodyear et al. had previously observed increased quantities of HSV when cultured on skin explants obtained from patients with AD and psoriasis compared to skin from normal individuals (Clin. Exp. Dermatol. 21:185, 1996). These experimental conditions were performed in the absence of many of these defense mechanisms. Eczema vaccinatum is a complication of smallpox vaccination seen within ten days after virus inoculation during primary immunization, also suggesting an important role for local, innate immune responses in restricting vaccinia viral replication.

Two major classes of antimicrobial peptides are produced by mammalian skin: β-defensins and cathelicidins. Both compounds have antimicrobial activities against bacterial and fungal pathogens A third class, α-defensins (e.g. HNP-1), found in human neutrophils and mucosal epithelial cells, also inhibit virus replication, particularly enveloped viruses including herpes simplex 1 and 2, cytomegalovirus, vesicular stomatitis virus and influenza A/WSN. Cathelicidins derived from bovine and porcine neutrophils also have antiviral (HSV) activity in vitro along with peptides of varying physical and chemical structures. However, the effect of antimicrobial peptides on vaccinia virus have not been reported. The mechanism of action for these cationic antimicrobial peptides is hypothesized to involve disruption of the microbial membrane and/or the penetration of the microbial membranes to interfere with intracellular functions. Keratinocytes are primary producers of these peptides in the skin following injury or an inflammatory skin response. However, neutrophils infiltrating into the pustules of smallpox could also play a role in limiting viral invasion by the production of anti-viral molecules such as α-defensin. The disclosure is based, in part, upon the discovery that keratinocytes in the inflammatory skin lesions of patients with AD are deficient in the cathelicidin LL-37 (i.e., LLGDFFRKSK EKIGKEFKR1 VQRIKDFLRN LVPRTES (SEQ ID NO:1)) and the β-defensin HBD-2 relative to psoriasis. The disclosure demonstrates the effect of cathelicidins, α-defensins, β-defensins, and control peptides for their effect on vaccinia virus replication in vitro. Because of ongoing debates regarding mass immunizations, a common model for immunization is the Wyeth strain, currently a vaccine strain available in the United States.

Eczema Vaccinatum (EV) is one of the major complications of small pox vaccination and occurs in patients with a history of atopic dermatitis (AD), a Th2-mediated skin disease. Recently it was found that AD skin is deficient in its ability to express certain endogenous antimicrobial peptides, also known as cathelicidins, such as LL-37 (Ong et al., NEJM 0.2002; 347:1151-60). This group of patients is known to be much more susceptible to serious complications of infection with vaccinia and related viruses. Vaccinia virus is used for small pox vaccination. At present, there is no method to identify individuals who may have reactions to small pox vaccination.

The term "antiviral" as used herein means that a peptide destroys, or inhibits or prevents the growth or proliferation of, a virus or a virus-infected cell.

As used herein, the term "cationic LL-37 peptide" refers to a chain of amino acids that is at least 37 amino acids in length and comprises a sequence as set forth in SEQ ID NO:1. A peptide is "cationic" if it has a pKa greater than 9.0. Typically, at least four of the amino acid residues of a cationic peptide are positively charged residues, e.g., lysine and arginine. "Positively charged" refers to the side chain of an amino acid residue that has a net positive charge at pH 7.0.

As used herein, the term "cationic CRAMP peptide" refers to a chain of amino acids that is at least 34 amino acids in length and comprises a sequence as set forth in SEQ ID NO:3 (GLLRKGGEKI GEKLKKIGQK IKNFFQKLVP QPEQ; SEQ ID NO:3).

The term "purified" as used herein refers to a peptide that is substantially free of other proteins, lipids, and nucleic acids (e.g., cellular components with which an in vivo-produced peptide would naturally be associated). Typically, the peptide is at least 70%, 80%, 90%, or more pure by weight.

The disclosure also includes analogs, derivatives, conservative variations, and cationic LL-37 peptide variants of SEQ ID NO:1 and cationic CRAMP peptide variants of SEQ ID NO:3, provided that the analog, derivative, conservative variation, or variant has a detectable antiviral activity. It is not necessary that the analog, derivative, variation, or variant have activity that is identical to the activity of SEQ ID NO:1 or SEQ ID NO:3.

As used herein a cationic antiviral peptide or variant is a cationic LL-37 peptide or variant, or a cationic CRAMP peptide or variant. A cationic antiviral peptide composition comprises a cationic LL-37 peptide or variant; a cationic CRAMP peptide or variant; or a combination of a cationic LL-37 peptide or variant, and a cationic CRAMP peptide or variant.

A cationic antiviral peptide variant is an antiviral peptide that is an altered form of SEQ ID NO:1 or SEQ ID NO:3. For example, the term "variant" includes a cationic antiviral peptide produced by the method disclosed herein in which at least one amino acid of a reference peptide is substituted in an expression library. The term "reference" peptide means a cationic LL-37 peptide of SEQ ID NO:1 or a cationic CRAMP peptide of SEQ ID NO:3 from which a variant, derivative, analog, or conservative variation is derived. Included within the term "derivative" is a hybrid cationic antiviral peptide that comprises SEQ ID NO:1 or 3 or variants thereof linked to a second peptide having a desired activity. Additional cationic antiviral peptide derivatives can be produced by adding one or a few (e.g., less than 5) amino acids to a cationic antiviral peptide (i.e., SEQ ID NO:1, SEQ ID NO:3) without completely inhibiting the antiviral activity of the peptide. In addition, C-terminal derivatives, e.g., C-terminal methyl esters, can be produced and are encompassed by the disclosure.

The disclosure also includes peptides that are conservative variations of those peptides. The term "conservative variation" as used herein denotes a peptide in which at least one amino acid is replaced by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acid, or glutamine for asparagine, and the like. Neutral hydrophilic amino acids that can be substituted for one another include asparagine, glutamine, serine and threonine. The term "conservative variation" also encompasses a peptide having a substituted amino acid in place of an unsubstituted parent amino acid; typically, antibodies raised to the substituted polypeptide also specifically bind the unsubstituted polypeptide.

The activity of the peptides of the disclosure can be determined using conventional methods known to those of skill in the art.

Peptides of the disclosure can be synthesized by commonly used methods such as those that include t-BOC or FMOC protection of alpha-amino groups. Both methods involve stepwise synthesis in which a single amino acid is added at each step starting from the C terminus of the peptide (See, Coligan, et al., Current Protocols in Immunology, Wiley Interscience, 1991, Unit 9). Peptides of the disclosure can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62, using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

The disclosure also includes isolated nucleic acids (e.g., DNA, cDNA, or RNA) encoding the peptides of the disclosure. Included are nucleic acids that encode analogs, mutants, conservative variations, and variants of the peptides described herein. For example, an LL-37 polynucleotide/nucleic acid of the disclosure comprises the sequence of SEQ ID NO:2. In one aspect, a polynucleotide encoding a cationic LL-37 peptide comprises SEQ ID NO:2 from nucleotide 540 to nucleotide 650.

```
  1 taaagcaaac cccagcccac accctggcag gcagccaggg atgggtggat caggaaggct (SEQ ID NO: 2)

61 cctggttggg cttttgcatc aggctcaggc tgggcataaa ggaggctcct gtgggctaga 121 gggaggcaga catggggacc atgaagaccc aaagggatgg ccactccctg gggcggtggt 181 cactggtgct cctgctgctg ggcctggtga tgcctctggc catcattgcc caggtcctca 241 gctacaagga agctgtgctt cgtgctatag atggcatcaa ccagcggtcc tcggatgcta 301 acctctaccg cctcctggac ctggacccca ggcccacgat ggatggggac ccagacacgc 361 caaagcctgt gagcttcaca gtgaaggaga cagtgtgccc caggacgaca cagcagtcac 421 cagaggattg tgacttcaag aaggacgggc tggtgaagcg gtgtatgggg acagtgaccc 481 tcaaccaggc caggggctcc tttgacatca gttgtgataa ggataacaag agatttgccc 541 tgctgggtga tttcttccgg aaatctaaag agaagattgg caaagagttt aaaagaattg 601 tccagagaat caaggatttt ttgcggaatc ttgtacccag gacagagtcc tagtgtgtgc 661 cctaccctgg ctcaggcttc tgggctctga gaataaact atgagagcaa tttcaaaaaa 721 aaaaaaaaaa aaaaaaaaa
```

In another example, a CRAMP polynucleotide/nucleic acid of the disclosure comprises the sequence of SEQ ID NO:4. In one aspect, a polynucleotide encoding a cationic CRAMP peptide comprises SEQ ID NO:4 from nucleotide 434 to nucleotide 532.

```
  1 TCAGTCTTGG GAACCATGCA GTTCCAGAGG GACGTCCCCT CCCTGTGGCT GTGGCGGTCA (SEQ ID NO: 4)

61 CTATCACTGC TGCTGCTACT GGGCCTGGGG TTCTCCCAGA CCCCCAGCTA CAGGGATGCT

121 GTGCTCCGAG CTGTGGATGA CTTCAACCAG CAGTCCCTAG ACACCAATCT CTACCGTCTC

181 CTGGACCTGG ATCCTGAGCC CCAAGGGGAC GAGGATCCAG ATACTCCCAA GTCTGTGAGG

241 TTCCGAGTGA AGGAGACTGT ATGTGGCAAG GCAGAGCGGC AGCTACCTGA GCAATGTGCC

301 TTCAAGGAAC AGGGGGTGGT GAAGCAGTGT ATGGGGGCAG TCACCCTGAA CCCGGCCGCT

361 GATTCTTTTG ACATCAGCTG TAACGAGCCT GGTGCACAGC CCPTTTCGGT TCAAGAAAAT

421 TTCCCGGCTG GCTGGACTTC TCCGCAAAGG TGGGGAGAAG ATTGGTGAAA AGCTTAAGAA

481 AATTGGCCAG AAAATTAAGA ATTTTTTTCA GAAACTTGTC CCTCAGCCAG AGTAGTAGGC

541 CTGCCTTGGC CTGTTTCTGG ATTCCCTAAA ATTATAAACT TGGTAAAAAA AA(A)$_n$
```

In one embodiment, the disclosure provides an isolated polynucleotide sequence encoding a cationic antiviral peptide or variant thereof. An exemplary cationic LL-37 peptide of the disclosure has an amino acid sequence as set forth in SEQ ID NO:1. Similarly, an exemplary cationic CRAMP peptide of the disclosure has an amino acid sequence as set forth in SEQ ID NO:3. Polynucleotide sequences encoding a peptide of SEQ ID NO:1 or variants thereof, or SEQ ID NO:3 or variants thereof include DNA, cDNA and RNA sequences. Such polynucleotides include naturally occurring, synthetic, and intentionally manipulated polynucleotides. For example, a cationic antiviral peptide or variant polynucleotide may be subjected to site-directed mutagenesis. A cationic antiviral peptide or variant polynucleotide includes sequences that are degenerate as a result of the genetic code. There are 20 natural amino acids, most of which are specified by more than one codon. Therefore, all degenerate nucleotide sequences are included so long as the amino acid sequence of a cationic antiviral peptide or variant encoded by the nucleotide sequence is functionally unchanged. Accordingly, a cationic antiviral polynucleotide includes (i) a polynucleotide encoding a cationic antiviral peptide or variant; (ii) a polynucleotide encoding SEQ ID NO:1 or a variant thereof, or SEQ ID NO:3 or a variant thereof; (iii) a polynucleotide comprising SEQ ID NO:2 or SEQ ID NO:4; (iv) a polynucleotide comprising SEQ ID NO:2 or SEQ ID NO:4, wherein T is U; and (v) a polynucleotide comprising a sequence that is complementary to (iii) and (iv) above. It will be recognized that a cationic antiviral polynucleotide, may be operably linked to a second heterologous polynucleotide such as a promoter or a heterologous sequence encoding a desired peptide or polypeptide sequence.

The term "isolated" as used herein refers to a nucleic acid that is substantially free of proteins, lipids, and other nucleic acids with which an in vivo-produced nucleic acids naturally associated. Typically, the nucleic acid is at least 70%, 80%, 90% or more pure by weight, and conventional methods for synthesizing nucleic acids in vitro can be used in lieu of in vivo methods. As used herein, "nucleic acid" refers to a polymer of deoxyribonucleotides or ribonucleotides, in the form of a separate fragment or as a component of a larger genetic construct (e.g., by operably linking a promoter to a nucleic acid encoding a peptide of the disclosure). Numerous genetic constructs (e.g., plasmids and other expression vectors) are known in the art and can be used to produce the peptides of the disclosure in cell-free systems or prokaryotic or eukaryotic (e.g., yeast, insect, or mammalian) cells. By taking into account the degeneracy of the genetic code, one of ordinary skill in the art can readily synthesize nucleic acids encoding the polypeptides of the disclosure. The nucleic acids of the disclosure can readily be used in conventional molecular biology methods to produce the peptides of the disclosure.

DNA encoding the cationic antiviral peptides of the disclosure can be inserted into an "expression vector." The term "expression vector" refers to a genetic construct such as a plasmid, virus or other vehicle known in the art that can be engineered to contain a nucleic acid encoding a polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a nucleic acid of the disclosure can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a nucleic acid into a cell by high voltage electric impulse. Additionally, nucleic acids can be introduced into host cells by protoplast fusion, using methods well known in the art. Suitable methods for transforming eukaryotic cells, such as electroporation and lipofection, also are known.

"Host cells" encompassed by of the disclosure are any cells in which the nucleic acids of the disclosure can be used to express the polypeptides of the disclosure. The term also includes any progeny of a host cell. Commonly used host cells of the disclosure include *E. coli, S. aureus* and *P. aeruginosa*.

Nucleic acids encoding the peptides of the disclosure can be isolated from a cell (e.g., a cultured cell), or they can be produced in vitro. A DNA sequence encoding a cationic antiviral peptide can be obtained by: 1) isolation of a double-stranded DNA sequence from genomic DNA; 2) chemical manufacture of a nucleic acid such that it encodes the cationic antiviral peptide of interest; or 3) in vitro synthesis of a double-stranded DNA sequence by reverse transcription of mRNA isolated from a donor cell (i.e., to produce cDNA). Among the standard procedures for isolating cDNA sequences of interest is the formation of plasmid or phage containing cDNA libraries that are derived from reverse transcription of mRNA in donor cells that have a high level of genetic expression. When used in combination with polymerase chain reaction technology, even rare gene products can be cloned.

The disclosure also provides a method for inhibiting the spread or infection of a virus by contacting the virus or a surface upon which a virus may be present with an inhibiting effective amount of a cationic antiviral peptide of the disclosure. The term "contacting" refers to exposing the virus to a cationic antiviral peptide so that the peptide can inhibit the spread of infectivity of a virus or kill the virus itself. For example, by adding a cationic antiviral peptide to a culture comprising a virus (e.g., vaccinia virus) one can measure the susceptibility of a culture to the infectivity of a virus in the presence and absence of a cationic antiviral peptide. Alternatively, contacting can occur in vivo, for example, by administering a cationic antiviral peptide to a subject that is susceptible to or afflicted with a viral infection. The administration includes topical as well as parenteral. "Inhibiting" or "inhibiting effective amount" refers to the amount of a cationic antiviral peptide that is sufficient to cause a viral inhibition or kill a virus. Examples of viruses that can be inhibited include herpesviridae (herpes simplex virus (HSV), *varicella*-zoster virus), vaccinia virus, Pappiloma virus and other viruses causing skin diseases. The method for inhibiting the viral infection can also include the contacting of a virus with a cationic antiviral peptide alone or in combination with one or more other antiviral agents.

A cationic antiviral peptide(s) of the disclosure can be administered to any host, including a human or non-human animal, in an amount effective to inhibit growth of a virus. Thus, the peptides are useful as antiviral agents.

Any of a variety of art-known methods can be used to administer the peptide to a subject. For example, a cationic antiviral peptide of the disclosure can be administered parenterally by injection or by gradual infusion over time. The peptide can be administered intravenously, intraperitoneally, intramuscularly, subcutaneously, intracavity, or transdermally. In another aspect, a cationic antiviral peptide of the disclosure may be formulated for topical administration (e.g., as a lotion, cream, spray, gel, or ointment). Examples of formulations in the market place include topical lotions, creams, soaps, wipes, and the like. It may be formulated into liposomes to reduce toxicity or increase bioavailability. Other methods for delivery of the peptide include oral methods that entail encapsulation of the peptide in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a peptide of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antiviral agents, anti-oxidants, cheating agents, inert gases and the like also can be included.

The disclosure provides a method for inhibiting viral infection and spread of such viruses as herpesviridae (herpes simplex virus (HSV), *varicella*-zoster virus), vaccinia virus, Pappiloma virus and other viruses causing skin diseases, as well as diseases and disorders associated with atopic dermatitis by administering a therapeutically effective amount of a cationic antiviral peptide of the disclosure to a subject who has, or is at risk of having, such an infection or disorder. The term "inhibiting" means preventing or ameliorating infectivity of a virus or a sign or symptoms of a disorder (e.g., atopic dermatitis). Examples of disease signs that can be ameliorated include skin sores and lesions associated with herpesviridae (herpes simplex virus (HSV), *varicella*-zoster virus), vaccinia virus, Pappiloma virus and other viruses causing skin infection such as those seen in atopic dermatitis. Examples of patients who can be treated in the disclosure include those at risk for, or those suffering from, a viral infection, such as those resulting from Herpesviridae (herpes simplex virus (HSV), *varicella*-zoster virus), vaccinia virus, Pappiloma virus and other viruses causing skin diseases. Those skilled in the art of medicine can readily employ conventional criteria to identify appropriate subjects for treatment in accordance with the disclosure.

The term "therapeutically effective amount" as used herein for treatment of a subject or patient afflicted with a disease or disorder means an amount of cationic antiviral peptide sufficient to ameliorate a sign or symptom of the disease. For example, a therapeutically effective amount can be measured as the amount sufficient to decrease the severity or number of sores/lesions associated with atopic dermatitis, herpes viral infection, and/or vaccinia virus infection. Generally, the optimal dosage of a cationic antiviral peptide will depend upon the disorder and factors such as the weight of the patient or subject, the type of viral infection, the progress of any related disease or disorder association with the virus and/or the like. Nonetheless, suitable dosages can readily be determined by one skilled in the art. If desired, the effectiveness of treatment typically can be measured by monitoring the level of viral titer or viral load in a patient or subject. A decrease in viral titer or load levels generally is correlated with amelioration of the disorder, infection and/or disease. Typically, a suitable dosage is 0.5 to 40 mg peptide/kg body weight, (e.g., 1 to 8 mg peptide/kg body weight).

If desired, a suitable therapy regime can combine administration of a peptide(s) of the disclosure with an additional antiviral agent and/or other therapeutic agents used to relieve symptoms associated with the viral infection. The peptide(s), inhibitor(s), and/or other therapeutic agents can be administered, simultaneously, but may also be administered sequentially. Typically, the cationic antiviral peptide and other agents are administered within 48 hours of each other (typically 2-8 hours). A "viral killing amount" of antiviral is an amount sufficient to achieve a virus-killing blood concentration or a viral-killing surface concentration in or on the patient or subject receiving the treatment. In accordance with its conventional definition, an "antiviral agent," as used herein, is a chemical or biologic substance that inhibits the growth of, spread of, or kills viral particles.

The cationic antiviral peptides of the disclosure can be used, for example, as preservatives or sterillants of materials susceptible to viral contamination. For example, the peptides can be used as preservatives in processed foods, as spray disinfectants commonly used in the household or clinical environment. The optimal amount of a cationic peptide of the disclosure for any given application can be readily determined by one of skill in the art.

In the present disclosure, a polynucleotide encoding a cationic antiviral peptide or variants can be inserted into a recombinant "expression vector." The term "expression vector" refers to a plasmid, virus or other vehicle known in the art that can be manipulated by insertion or incorporation of a nucleic acid encoding a cationic antiviral peptide or variant. Typically, expression vectors are plasmids that contain a promoter for directing transcription of the inserted genetic sequence.

If desired, the expression vector can encode a "carrier peptide," which typically is produced as a fusion with the amino or carboxy terminus of the peptide variant. Typically, the carrier peptide is sufficiently anionic such that the positive charge associated with the cationic peptide is overcome and the resulting fusion peptide has a net charge that is neutral or negative. The anionic carrier peptide can correspond in sequence to a naturally-occurring protein or can be entirely artificial in design. Functionally, the carrier peptide may help stabilize the cationic peptide and protect it from proteases, although the carrier peptide need not be shown to serve such a purpose. Similarly, the carrier peptide may facilitate transport of the fusion peptide. Examples of carrier peptide that can be utilized include anionic pre-pro peptides and anionic outer membrane peptides. Examples of carrier peptides include glutathione-5-transferase (GST), protein. A of *Staphylococcus aureus*, two synthetic IgG-binding domains (ZZ) of protein A, outer membrane protein F of *Pseudomonas aeruginosa*, and the like. The disclosure is not limited to the use of these peptides as carriers; others suitable carrier peptides are known to those skilled in the art. Alternatively, the carrier peptide can be omitted altogether. In another aspect, a linker moiety comprising a protease cleavage site may be operably linked to a cationic antiviral peptide or variant of the disclosure. Because protease cleavage recognition sequences generally are only a few amino acids in length, the linker moiety can include the recognition sequence within flexible spacer amino acid sequences, such as GGGGS (SEQ ID NO:5). For example, a linker moiety including a cleavage recognition sequence for Adenovirus endopeptidase could have the sequence GGGGGGSMFG GAKKRSGGGG GG (SEQ ID NO:6).

Any of various art-known methods for protein purification can be used to isolate the peptides of the disclosure. For example, preparative chromatographic separations and immunological separations (such as those employing monoclonal or polyclonal antibodies) can be used. Carrier peptides can facilitate isolation of fusion proteins that include the peptides of the disclosure. For example, glutathione-5-transferase (GST) allows purification with a glutathione agarose affinity column. When either Protein A or the ZZ domain from *Staphylococcus aureus* is used as the carrier protein, purification can be accomplished in a single step using an IgG-sepharose affinity column. The poprF-peptide, which is the N-terminal half of the *P. aeruginosa* outer membrane protein F, can readily be purified because it is the prominent protein species in outer membrane preparations. If desired, the fusion peptides can be isolated by using reagents that are specifically reactive with (e.g., specifically bind) the cationic antiviral peptide of the fusion peptide. For example, monoclonal or polyclonal antibodies that specifically bind a cationic antiviral peptide can be used in conventional purification methods. Techniques for producing such antibodies are well known in the art.

In practicing the disclosure, it may be advantageous to include a "spacer DNA sequence" in the expression vectors. As used herein, "spacer DNA sequence" refers to any coding sequence located between the sequence encoding the carrier peptide and the sequence encoding the cationic antiviral peptide. While not wanting to be bound to a particular theory, it is believed that the spacer DNA sequence, when translated, can create a "hinge-like" region that allows the negatively charged residues of the anionic carrier peptide and the positively charged residues of the subject cationic peptide to interact, thereby inhibiting positive charge effects.

If desired, the spacer DNA sequence can encode a protein recognition site for cleavage of the carrier peptide from the fusion peptide. Examples of such spacer DNA sequences include, but are not limited to, protease cleavage sequences, such as that for Factor Xa protease, the methionine, tryptophan and glutamic acid codon sequences, and the pre-pro defensin sequence. Factor Xa is used for proteolytic cleavage at the Factor Xa protease cleavage sequence, while chemical cleavage by cyanogen bromide treatment releases the peptide at the methionine or related codons. In addition, the fused product can be cleaved by insertion of a codon for tryptophan (cleavable by o-iodosobenzoic acid) or glutamic acid (cleavable by *Staphylococcus* protease). Insertion of such spacer DNA sequences is not a requirement for the production of functional cationic peptides, such sequences can enhance the stability of the fusion peptide. The pre-pro defensin sequence is negatively charged; accordingly, it is envisioned within the disclosure that other DNA sequences encoding negatively charged peptides also can be used as spacer DNA sequences to stabilize the fusion peptide.

In another aspect, the disclosure provides knockout non-human animals that are useful to screen potential antiviral agents and agents useful for treating such diseases and disorders as atopic dermatitis.

Due to their increased risk of eczema vaccinatum, patients with atopic dermatitis cannot be inoculated with the smallpox vaccine unless there is imminent risk of exposure to smallpox. As a model to study the potential in vivo significance of LL-37 deficiency, CRAMP Cnlp knockout mice known to lack expression of CRAMP, a close murine ortholog of cathelicidin human LL-37 were developed and used. Importantly these mice generated a significantly greater number of pox skin lesions than seen in wild type isogenic control mice. The two mice that did not generate pox skin lesions died within two days of septic shock following smallpox vaccination. The recent reports of human deaths following vaccination and the deaths of two Cnlp−/− animals reiterate the importance the need to test the roles of antimicrobial peptides as components of innate defense in experimental animals followed by application of these experimental findings to their role in human disease.

These in vitro and in vivo observations suggest that the increased susceptibility of atopic dermatitis patients to eczema vaccinatum may be due to a deficiency of cathelicidin. LL-37 deficiency, as detected by real time (rt) PCR predisposes individuals to eczema vaccination and other effects of small pox virus. Evaluation of expression of cathelicidin in individuals with atopic dermatitis (15% lifetime prevalence in the general population) can be used in predetermination of the risk of vaccination. The disclosure is the discovery that animals, specifically mice, lacking cathelicidin are more easily infected with vaccinia virus. The disclosure is the discovery that the cathelicidin parent peptides LL-37 and CRAMP are able to kill vaccinia virus. Other cationic antimicrobial peptides tested to date do not kill vaccinia (e.g. HBD-2).

"Knock-out" refers to partial or complete suppression of the expression of a protein encoded by an endogenous DNA sequence in a cell. The "knock-out" can be affected by targeted deletion of the whole or part of a gene encoding a protein, in an embryonic stem cell. As a result, the deletion may prevent or reduce the expression of the protein in any cell in the whole animal in which it is normally expressed.

"Transgenic animal" refers to an animal to which exogenous DNA has been introduced while the animal is still in its embryonic stage. In most cases, the transgenic approach aims at specific modifications of the genome, e.g., by introducing whole transcriptional units into the genome, or by up- or down-regulating pre-existing cellular genes. The targeted character of certain of these procedures sets transgenic technologies apart from experimental methods in which random mutations are conferred to the germline, such as administration of chemical mutagens or treatment with ionizing solution.

Knocking out the homologue of LL-37 in an animal model (e.g., CRAMP) in mice would create highly sensitive animal models for the detection of viral infection and as models for atopic dermatitis, and related diseases and disorders such as increased susceptibility to viral and bacterial infections. Thus, CRAMP knockout animals, for example, would be highly sensitive to viral and bacterial infections, and could accordingly be used to screen for such infections and for drugs or biologics useful in treating or reducing the risk of infection.

Accordingly, the disclosure provides non-human transgenic animals. Such animals are useful for studying the function and/or activity of cathelicidin including LL-37 and related homologues (e.g., CRAMP) and for identifying and/or evaluating modulators of a cathelicidin activity or drugs or biologics that are useful in treating disorders associated with a cathelicidin deficiency. As used herein, a "transgenic animal" is a non-human animal, typically a mammal, such as a rodent (e.g., a rat or mouse), in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which one or more of an endogenous cathelicidin genes, e.g., a LL-37 homologue such as CRAMP, has been altered by, e.g., by homologous recombination between the endogenous gene and an exogenous DNA molecule introduced into a cell of the animal, e.g., an embryonic cell of the animal, prior to development of the animal.

Various methods to make the transgenic animals can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is typically used for avian species, for example as described in U.S. Pat. No. 5,162,215. If micro-injection is to be used with avian species, however, a published procedure by Love et al., (Biotechnology, Jan. 12, 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization. The "non-human animals" include bovine, porcine, rats, mice, ovine and avian animals (e.g., cow, pig, sheep, chicken). The "transgenic non-human animals" of the disclosure are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal that includes exogenous genetic material within all of its cells. A "transgenic" animal can be produced by cross-breeding two chimeric animals that include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the disclosure, the transgene is digested and purified free from any vector DNA e.g. by gel electrophoresis. In some aspect, the transgene includes an operatively associated promoter that interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, typical promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927-6931, 1985; Van der Putten, et al., Proc. Natl. Acad. Sci USA 82:6148-6152, 1985). Transfection is easily and efficiently obtained by culturing the blastomeres on a monolayer of virus-producing cells (Van der Putten, supra; Stewart, et al., EMBO J. 6:383-388, 1987). Alternatively, infection can be performed at a later stage. Virus or virus-producing cells can be injected into the blastocoele (D. Jahner et al., Nature 298:623-628, 1982). Most of the founders will be mosaic for the transgene since incorporation occurs only in a subset of the cells that formed the transgenic nonhuman animal. Further, the founder may contain various retroviral insertions of the transgene at different positions in the genome that generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. Nature 292:154-156, 1981; M. O. Bradley et al., Nature 309: 255-258, 1984; Gossler, et al., Proc. Natl. Acad. Sci USA 83: 9065-9069, 1986; and Robertson et al., Nature 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468-1474, 1988). "Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA, which is inserted by artifice into a cell, and becomes part of the genome of the organism (i.e., either stably integrated or as a stable extrachromosomal element), which develops from that cell. Such a transgene may include a gene that is partly or entirely heterologous (i.e., foreign) to the transgenic organism, or may represent a gene homologous to an endogenous gene of the organism. Included within this definition is a transgene created by the providing of an RNA sequence, which is transcribed into DNA and then incorporated into the genome. The transgenes of the disclosure include DNA sequences that encode cathelicidin and related homologues (e.g., CRAMP), and include sense and antisense polynucleotides, which may be expressed in a transgenic non-human animal. Also included are polynucleotides that have overlapping sequences (i.e., substantially identical sequences) at the 5' and 3' termini of gene located in the genome of the organism. Such a polynucleotide includes a non-identical sequence between the 5' and 3' termini. When incorporated into a cell such a polynucleotide incorporates at a defined location in the genome and thus disrupts an endogenous gene thereby knocking out the gene in the transgenic organism. Accordingly, the term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out." Specifically provided by the disclosure is a mouse model lacking CRAMP expression.

The transgene to be used in the practice of the subject disclosure is a DNA sequence comprising a modified CRAMP coding sequence. In one embodiment, the CRAMP gene is disrupted by homologous targeting in embryonic stem cells. The disruption or deletion may be accompanied by insertion of or replacement with other DNA sequences, such as a non-functional CRAMP sequence. In other embodiments, the transgene comprises DNA antisense to the coding sequence for CRAMP. In another embodiment, the transgene comprises DNA encoding an antibody or receptor peptide sequence that is able to bind to CRAMP. The DNA and peptide sequences of CRAMP are known in the art.

The disclosure also includes animals having heterozygous mutations in cathelicidin and related homologues (e.g., CRAMP). A heterozygote would likely have increased susceptibility to viral infection or atopic dermatitis.

After an embryo has been microinjected, colonized with transfected embryonic stem cells or infected with a retrovirus containing the transgene (except for practice of the subject disclosure in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. The serum levels or skin levels of a cathelicidin (e.g., CRAMP) can also be measured in the transgenic animal to establish appropriate expression. Expression of the cathelicidin (e.g., CRAMP) transgenes, thereby decreasing the cathelicidin in the tissue and serum levels of the transgenic animals and consequently increasing viral susceptibility and risk of atopic dermatitis in these animals.

The disclosure provides a method of identifying the risk of dermatitis in the skin. In a typical embodiment the present disclosure relates to a method for identifying the risk or propensity of developing atopic dermatitis by detecting a polynucleotide encoding LL-37 obtained from the skin and comparing the level of LL-37 polynucleotide to a standard sample.

Samples from a tissue may be isolated by any number of means well known in the art. In a typical embodiment the disclosure provides a non-invasive method for obtaining a skin sample for use in isolating nucleic acids to identify the risk or presence of a dermatitis. In this embodiment epidermal cells of the skin are scraped with a rigid instrument, for example a sterile #15 scalpel, however, it will be recognized that any number of rigid instruments capable of removing only the surface layer (i.e., stratum corneum) of the skin may be used. Alternatively, instead of scraping the skin, the skin's epidermal layer may be removed by using an adhesive tape, for example, Duct tape (333 Duct tape, Nashua tape products) or Scotch® tape (3M Scotch 810, St. Paul, Minn.). However, the typical method is to use D-SQUAME® (CuDerm, Dallas, Tex.) to strip the skin cell layer. In this embodiment the skin is stripped with the tape and the stripped cells are then recovered from the scalpel, tape or other item. For example, tape used to obtain skin cells may be centrifuged in a sterile microfuge tube containing lysis buffer. In the case of the scalpel the cells may be transferred to a sterile petri dish and lysed therein with lysis buffer. The same lysis buffer may be reused for each piece of tape or scalpel used at a single skin site. For certain applications, the tape stripping method can be combined with the scraping method for removing cells from the skin. The sample obtained may then be further processed, for example to isolate polynucleotides. Polynucleotides can be isolated from the lysed cells by any number of means known to those skilled in the art. For example, a number of commercial products are available for isolating polynucleotides, including but not limited to, TriReagent (Molecular Research Center, Inc, Cincinnati, Ohio) may be used. The isolated polynucleotides can then be tested or assayed for LL-37 polynucleotides. The DNA or RNA may be single stranded or double stranded. When RNA is obtained, enzymes and conditions optimal for reverse transcribing the template to DNA can be used. Alternatively, the RNA can be subjected to RNAse protection assays. A DNA-RNA hybrid that contains one strand of each may also be used. A mixture of polynucleotides may also be employed, or the polynucleotides produced in a previous amplification reaction, using the same or different primers may be so used. In the instance where the polynucleotide sequence is to be amplified the polynucleotide sequence may be a fraction of a larger molecule or can be present initially as a discrete molecule, such that the specific sequence is the entire nucleic acid. It is not necessary that the sequence to be amplified be present initially in a pure form; it may be a minor fraction of a complex mixture, such as contained in whole human DNA. In addition, RNAse protection assays may be used if RNA is the polynucleotides obtained from the sample. In this procedure, a labelled antisense RNA probe is hybridized to the complementary polynucleotide in the sample. The remaining unhybridized single-stranded probe is degraded by ribonuclease treatment. The hybridized, double stranded probe is protected from RNAse digestion. After an appropriate time, the products of the digestion reaction are collected and analyzed on a gel (see for example Ausubel et al., CURRENT PROTOCOLS IN MOLECULAR BIOLOGY, section 4.7.1 (1987)). As used herein, "RNA probe" refers to a ribonucleotide capable of hybridizing to RNA in a sample of interest. Those skilled in the art will be able to identify and modify the RNAse protection assay specific to the polynucleotides to be measured, for example, probe specificity may be altered, hybridization temperatures, quantity of nucleic acids and the like. Additionally, a number of commercial kits are available, for example, RiboQuant™ Multi-Probe RNAse Protection Assay System (Pharmingen, Inc., San Diego, Calif.).

In another embodiment, the polynucleotide in the sample may be analyzed by Northern or Southern blot. In this technique the polynucleotides are separated on a gel and then probed with complementary polynucleotides the hybridize to an LL-37 polynucleotide in the sample. For example, RNA is separated on a gel transferred to nitrocellulose and probed with complementary DNA to an LL-37 sequence. The complementary probe may be labelled radioactively, chemically and the like. Hybridization of the probe is indicative of the presence of the LL-37 polynucleotide in the sample.

Detection of a polynucleotide encoding LL-37 may be performed by standard methods such as size fractionating the nucleic acids. Methods of size fractionating the DNA and RNA are well known to those of skill in the art, such as by gel electrophoresis, including polyacrylamide gel electrophoresis (PAGE). For example, the gel may be a denaturing 7 M or 8 M urea-polyacrylamide-formamide gel. Size fractionating the nucleic acid may also be accomplished by chromatographic methods known to those of skill in the art.

The detection of polynucleotides may optionally be performed by using radioactively labelled probes. Any radioactive label may be employed which provides an adequate signal. Other labels include ligands, which can serve as a specific binding pair member for a labelled ligand, and the like. The labelled preparations are used to probe nucleic acid by the Southern or Northern hybridization techniques, for example. Nucleotides obtained from samples are transferred to filters that bind polynucleotides. After exposure to the labelled nucleic acid probe, which will hybridize to nucleotide fragments containing target nucleic acid sequences, the binding of the radioactive probe to target nucleic acid fragments is identified by autoradiography (see Genetic Engineering, 1, ed. Robert Williamson, Academic Press (1981), pp. 72-81). The particular hybridization technique is not essential to the disclosure. Hybridization techniques are well known or easily ascertained by one of ordinary skill in the art. As improvements are made in hybridization techniques, they can readily be applied in the method of the disclosure.

The polynucleotides encoding LL-37 may be amplified before detecting. The term "amplified" refers to the process of making multiple copies of the nucleic acid from a single polynucleotide molecule. The amplification of polynucleotides can be carried out in vitro by biochemical processes known to those of skill in the art. The amplification agent may be any compound or system that will function to accomplish the synthesis of primer extension products, including enzymes. Suitable enzymes for this purpose include, for example, E. coli DNA polymerase I, Taq polymerase, Klenow fragment of E. coli DNA polymerase I, T4 DNA polymerase, other available DNA polymerases, polymerase muteins, reverse transcriptase, ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis will be initiated at the 3' end of each primer and proceed in the 5' direction along the template strand, until synthesis terminates, producing molecules of different lengths. There may be amplification agents, however, that initiate synthesis at the 5' end and proceed in the other direction, using the same process as described above. In any event, the method of the disclosure is not to be limited to the embodiments of amplification described herein.

One method of in vitro amplification which can be used according to this disclosure is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. The polymerase chain reaction is used to detect the presence of polynucleotides encoding LL-37 in the sample. Many polymerase chain methods are known to those of skill in the art and may be used in the method of the disclosure. For example, DNA can be subjected to 30 to 35 cycles of amplification in a thermocycler as follows: 95° C. for 30 sec, 52° to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54-58° C. for 1 min, an extension step at 70° C. for 1 min and a final extension step at 70° C.

The primers for use in amplifying the polynucleotides of the disclosure may be prepared using any suitable method, such as conventional phosphotriester and phosphodiester methods or automated embodiments thereof so long as the primers are capable of hybridizing to a polynucleotide encoding an LL-37. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the disclosure are complementary to each strand of an LL-37 polynucleotide and will be based upon the polynucleotide sequence as set forth in SEQ ID NO:2. The term "complementary" means that the primers must hybridize with their respective strands under conditions which allow the agent for polymerization to function. In other words, the primers that are complementary to the flanking sequences hybridize with the flanking sequences and permit amplification of the nucleotide sequence. Typically, the 3' terminus of the primer that is extended has perfectly base paired complementarity with the complementary flanking strand.

Those of ordinary skill in the art will know of various amplification methodologies which can also be utilized to increase the copy number of target nucleic acid. The polynucleotides detected in the method of the disclosure can be further evaluated, detected, cloned, sequenced, and the like, either in solution or after binding to a solid support, by any method usually applied to the detection of a specific nucleic acid sequence such as another polymerase chain reaction, oligomer restriction (Saiki et al., Bio/Technology 3: 1008-1012 (1985)), allele-specific oligonucleotide (ASO) probe analysis (Conner et al., Proc. Natl. Acad. Sci. USA 80: 278 (1983), oligonucleotide ligation assays (OLAs) (Landegren et al., Science 241: 1077 (1988)), RNAse Protection Assay and the like. Molecular techniques for DNA analysis have been reviewed (Landegren et al, Science, 242: 229-237 (1988)). Following DNA amplification, the reaction product may be detected by Southern blot analysis, without using radioactive probes. In such a process, for example, a small sample of DNA containing a the polynucleotides obtained from the tissue or subject are amplified, and analyzed via a Southern blotting technique. The use of non-radioactive probes or labels is facilitated by the high level of the amplified signal. In a one embodiment of the disclosure, one nucleoside triphosphate is radioactively labelled, thereby allowing direct visualization of the amplification product by autoradiography. In another embodiment, amplification primers are fluorescent labelled and run through an electrophoresis system. Visualization of amplified products is by laser detection followed by computer assisted graphic display.

Simple visualization of a gel containing the separated products may be utilized to determine the presence, risk or severity of a dermatitis. However, other methods known to those skilled in the art may also be used, for example scanning densitometry, computer aided scanning and quantitation and others.

Thus, using the methods described above, one can non-invasively obtain a sample of tissue from a subject suspected of having or at risk of having a dermatitis (e.g., atopic dermatitis).

In another embodiment the disclosure provides a way of screening for agents or identifying agents which may cause or prevent a dermatitis. In this method, cells of the skin, such as epidermal cells, including keratinocytes and melanocytes, or dermal cells, such as fibroblasts, are contacted with a agent under conditions which would induce or inhibit a dermatitis reaction. The conditions under which contact is made are variable and will depend upon the type of agent, the type and amount of cells in the skin to be tested, the concentration of the agent in the sample to be tested, as well as the time of exposure to the agent. The skill in the art in determining the proper conditions under which a agent may cause a dermatitis are known and would require only routine experimentation. Polynucleotides are then isolated from the cells which have been exposed to the agent and quantitated as described above to measure a change in LL-37 in the sample compared to a control or standard sample.

The following examples are intended to illustrate but not limit the disclosure. While they are typical of those that might be used, other procedures known to those skilled in the art may alternatively be used.

EXAMPLES

Virus source and Culture. The Wyeth strain was obtained from the Centers for Disease Control and Prevention. HeLa S3 (ATCC accession no. CCK-2.2), human adenocarcinoma, cells were grown to confluence in RPMI media supplemented with 10% Fetal Calf Sera for use of propagation of vaccinia virus. The cells were rinsed and overlaid with RPMI-2.5% FCS then inoculated with $5\times10^6$ PFU/T-175 flask and incubated at 37° C. in 5% $CO_2$ for 3 days. Virus was harvested after disruption of cells yielding infectious virions in the form of intracellular mature virions (IMV).

Animals. All strains of mice are from The Jackson Laboratory, Bar Harbor, Me. All protocols are directed by the guidelines stated in Institutional Animal Care and Use Committee approved protocols AS 2616-05 and AS 2596. This institution has an Animal Welfare Assurance number (A3026-1) on file with the Office of Protection from Research Risks. $2\times10^5$ PFUs of the virus were inoculated by scarification with 15 pricks into the skin of mice. C57/Bl6J and BALB/c were used for comparison with previous reports, 129x1/SvJ background animals were compared to the test homozygous CRAMP knock-out ($Cnlp^{-/-}$) mice, discussed more fully elsewhere herein. Previous reports using C57Bl/6J and BALB/c allowed comparison of the experiments described herein. The 129/SvJ animals were used as specific controls for the CRAMP knockout animals.

Peptide Preparations. Human and murine cathelicidins (LL-37 and CRAMP, respectively), and the control peptide 8044 (GLNGPDIYKGUYQFKSVEFD; SEQ ID NO:7) were synthesized via solid-phase t-BOC chemistry using standard methodology and purified to homogeneity via HPLC. HNP-1 was purified to homogeneity as assessed by acid-urea PAGE from bronchiectatic sputum using FPLC and HPLC. Beta-defensins HBD-1 and HBD-2 were produced from baculovirus-infected insect cells, and purified by HPLC to homogeneity. The identity of LL-37 and HNP-1 were confirmed by mass spectroscopy. The antimicrobial activity of control, CRAMP, and LL-37 peptides were confirmed against *E. coli* ML-35P, and found to be within reported parameters. Since the antimicrobial activity of β-defensins depends on assembly of disulfide bonds in the native conformation, these observations support functional correct disulfide bonding in the synthetic β-defensins used in the study. The control peptide 8044 had no antimicrobial activity against ML-35P. Peptide 8044 was chosen from a library of existing peptides for use as a control for the antimicrobial peptides tested in these studies based on size, overall hydrophobicity, and charge similarities with test peptides, yet it had no sequence identity with the test peptides.

HNP-1 was purified to homogeneity as assessed by acid-urea PAGE from bronchiectatic sputum using fast protein liquid chromatography and HPLC. HBD-1 and HBD-2 were produced from baculovirus-infected insect cells and purified by HPLC to homogeneity. The purities of HBD-1 and HBD-2 were confirmed by HPLC, which showed single peaks eluting at 31.3 and 37% acetonitrile, respectively, on a gradient of 0-41% acetonitrile in 0.1% trifluoroacetic acid. The identities of LL-37 and HNP-1 were confirmed by mass spectroscopy. The concentrations of antimicrobial and control peptides used in these experiments ranged from 0-50 μM, which corresponds to 0.20-2.25 μg/ml of LL-37, 0.19-2.0 μg/ml CRAMP, 0.16-1.7 μg/ml HNP-1, 0.2-2.2 μg/ml HBD-2, and 0.1-1.1 μg/ml 8044.

Anti-viral assays. $2\times10^5$/well BS-C-1 (ATCC accession no. CCL-26), African green monkey kidney cells were seeded in 24 well tissue culture plates in MEM-10% FCS, Pen/Strep and allowed to grow overnight before having the supernatant removed and replaced with MEM-2.5% FCS for virus incubation. The BS-C-1 cells were used for the quantitative estimates because they present uniform plaques. HeLa S3 are routinely used for preparations of virus stock as they give consistently high yields of virus, but due to their rounded morphology, do not present uniform plaques.

Peptides were diluted to the proper concentrations in 0.01× tryptic soy broth containing 10 mM sodium phosphate buffer, pH=7.4. Virus diluted in the same buffer was added to the peptides, and both were incubated for 24 hours, 37° C. 20 µl of the peptide/virus mixture was added to cells in 0.5 ml MEM-2.5% FCS and allowed to infect for 24 hours for RNA analysis, or 48 hours for plaque development. For the plaque assay, the medium was removed and wells were overlaid with 0.5 ml 4% buffered formalin, allowed to fix for ten minutes at room temperature and the liquid removed. 0.5 ml 0.1% crystal violet in PBS was added to the wells, five minutes at room temperature then aspirated and the wells were air-dried. The most accurate results with the virus alone formed 50-80 plaques per well.

Electron Microscopy. Virus stock ($10^8$ PFU) was concentrated by ultracentrifugation at 50,000 RPM, 4° C., for 60 minutes in a TL-100 rotor. The media was removed, and the pellet washed with 1.0 ml 0.01×TSB/10 mM Phosphate Buffer and spun again. The final pellet was re-suspended in 0.2 ml final volume in buffer and peptide was added at starting concentrations of 5, 25, and 50 mM. The mixture was incubated at 37° C. for 24 hours, followed by addition of an equal volume of 3% glutaraldehyde. The samples were stored at 4° C. until transmission electron microscopy with a Phillip's CM-10 could be performed at the Electron Microscopy Laboratory at National Jewish.

Vaccinia Gene Expression. Vaccinia gene expression was evaluated using quantitative real time RT-PCR. BS-C-1 cells were cultured in 24-well plates at a concentration of $2 \times 10^5$ cells/well. Twenty-four hours following culturing, virus and peptide were added to corresponding wells and allowed to incubate for an additional 24 hours. RNA was isolated from cultured cells using the RNeasy Mini Kit (Qiagen, Valencia, Calif.) according to manufacturer's guidelines. Real-time PCR was performed using an ABI 7700 Sequence Detection system (Applied Biosystems, Foster City, Calif.). The primer sequences that were used to assay for the vaccinia gene transcripts are: Forward, 5'-GCCAATGAGGGTTCGAGTTC-3' (SEQ ID NO:8) and Reverse, 5'-CAACATCCCGTCGT-TCATCA-3' (SEQ ID NO:9). This region of the genome encodes a subunit of a DNA-directed RNA polymerase expressed within two hours of viral entry. The TaqMan probe was purchased from Applied Biosystems: 5' labelled with 6-carboxyfluorescein (FAM) and 3'-labeled with 6-carboxy-tetramethylrhodamine (TAMRA). Amplification reactions were performed in MicroAmp optical tubes (Applied Biosystems) in a 25 ml volume containing 2× TaqMan Master Mix (Applied Biosystems), 900 nM forward primer, 900 nM reverse primer, 200 nM probe, and the template RNA. Thermal cycling conditions were: 50° C. for two minutes, 95° C. for ten minutes for one cycle. Subsequently 40 cycles of amplification were performed at 94° C. for 15 seconds and 60° C. for one minute. In order to quantitatively express the levels of vaccinia virus in BS-C-1 cells, a standard curve was generated using cDNA from purified vaccinia virus.

Statistical Analyses. Statistical comparisons of the reduction in PFUs and mRNA were made using the Excel program for the two-tailed T test. Analyses of viral structural alterations were performed using the Fisher's exact test (StatXact 4, Cytel Software). Mean MBC were determined from three independent experiments for each peptide.

Figure 2:
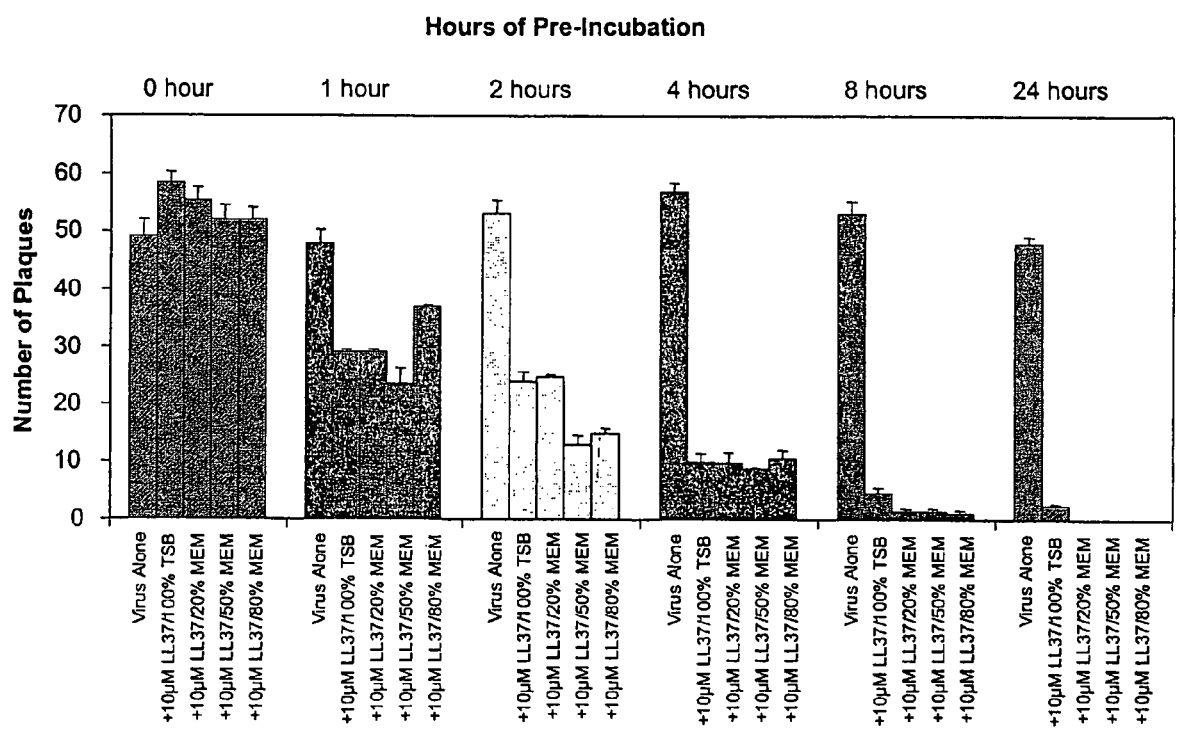
FIG. 2 shows plaque forming units of vaccinia virus following incubation with LL-37 at different salt concentrations for varying time periods: All conditions used 10 µM LL-37 for comparison of salt and time conditions. 0.01× Tryptic Soy Broth, 10 mM NaPO$_4$ (TSB) contains 0 mM NaCl, while 20% MEM contains 20.68 mM NaCl, 50% MEM contains 51.70 mM NaCl and 80% MEM contains 82.75 mM NaCl. Statistical comparisons address differences between no NaCl and increasing salt concentrations by decreasing plaque formation.

FIG. 1 demonstrates a concentration-dependent inhibition (p<0.001) of vaccinia virus replication following infection with a virion preparation consisting primarily of intracellular mature virions (IMV) that had been preincubated with cathelicidins LL-37 or CRAMP. In contrast, HNP-1, HBD-2, and the control peptides did not inhibit virus replication, although HNP-1 and the HBDs were active against *E. coli*. In previous reports, salt concentration and incubation time with target organism were shown to impact the function of AMPs in in vitro experiments. FIG. 2 describes the effect of varying salt concentration and exposure time on LL-37 activity, the only peptide shown to affect viral replication. At least one hour of contact with vaccinia at low (20% MEM) to high salt (80% MEM) was required to detect antiviral activity. Increasing concentrations of salts present in MEM tissue culture medium did not inhibit antiviral activity after 2 hr incubation, but the effect was lost after 4 hours of preincubation.

Figure 3:
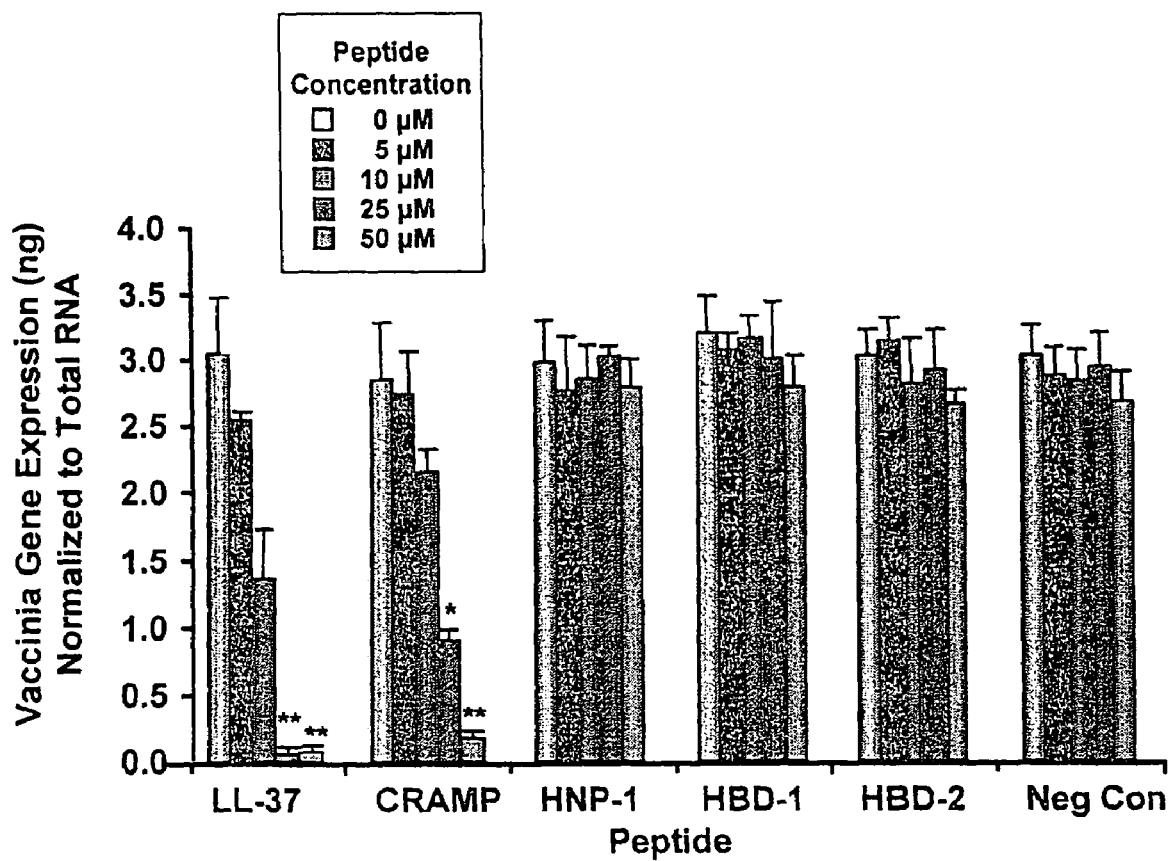
FIG. 3 shows quantity of vaccinia mRNA in tissue culture cells following incubation of virus prior to culture with antimicrobial and control peptides. P values compare vaccinia mRNA as measured by real time PCR to reduction in viral message at varying concentrations of the individual peptides. *P<0.05; **P<0/001. These data represent two separate experiments with four replicates per condition.

Quantitation of vaccinia mRNA in tissue culture cells by real time PCR under the conditions used for the plaque assays showed inhibition of viral mRNA expression (FIG. 3). The amount of viral mRNA in the tissue culture cells decreased in proportion to the concentration of LL-37 and CRAMP. Although LL-0.37 is not minimally expressed in normal skin keratinocytes (18), it is abundantly expressed after viral infection and the effective concentrations were equivalent to tissue levels found in human psoriatic skin or normal skin after injury.

Figure 4:
FIG. 4 shows transmission electron micrographs (22,000× magnification) of vaccinia virions before (A) and after incubation with (B) LL-37 at 5 μM final concentration, (C) LL-37 at 25 μM final concentration or (D) LL-37 at 50 μM final concentration, 200× additional magnification of virion displayed. Arrows in (B), (C), and (D) identify disrupt ions of the internal and outer bilayers of the IMV.

Electron microscopy of virions exposed to LL-37, α-defensin HNP-1, and control peptides demonstrated a concentration-dependent effect of only LL-37 on the structure of the IMV, including loss of integrity of the double-layered external envelope as well as that of the internal structure (FIG. 4). These electron microscopy studies suggest that LL-37 has direct effects on the integrity of the vaccinia viral membrane structure. In contrast, α-defensins and control peptides did not have an effect on virion structure. Examination of untreated virions did not identify similar structural changes, thus lessening the possibility that apparent alterations in structure are due to sectioning artifacts. A dose-dependent effect of in vitro incubation of LL-37 on the numbers and percentages of altered virions was found (see Table 1).

TABLE 1

Numbers and percentages of altered virions following exposure to LL-37*

| LL-37 (µM) | Altered virions/virion number | (%) |
|---|---|---|
| 0 | 1/23 | 4% |
| 5 | 19/28 | 67% |
| 25 | 27/30 | 90% |
| 50 | 39/41 | 95% |

*25 µM HNP-1 and control peptides did not alter virion structure

Figure 5:
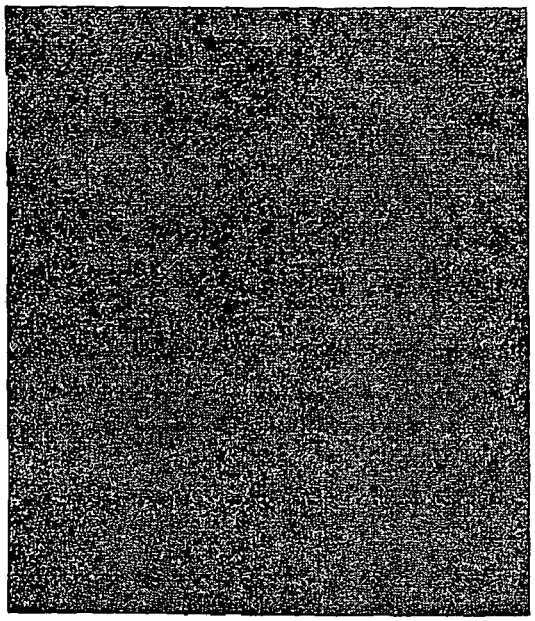
FIG. 5 shows the generation of vaccinia pox lesion in CRAMP KO mice. (A) Inoculation in control mouse ten days after scarification was negative. (B) CRAMP. KO; Ten days after scarification with vaccine virus developed pox lesion.
Figure 5:
Figure 6:
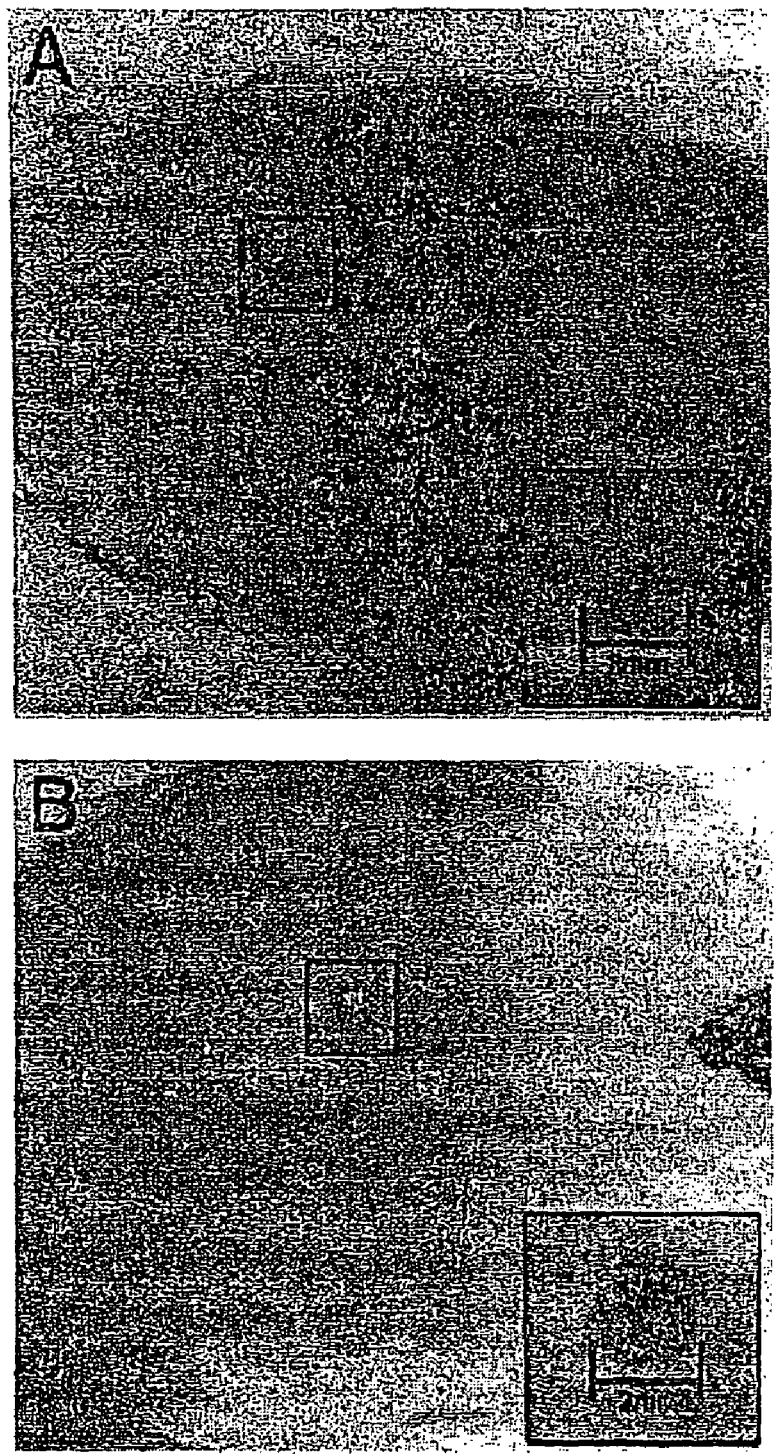
FIG. 6 shows the generation of vaccinia pox lesion in CRAMP knockout mice. (A) Inoculation in a representative control mouse; 10 days after scarification, the reaction was negative. (B) Inoculation in a representative CRAMP KO mouse; 10 days after scarification with vaccine virus, the animal developed a pox lesion. The boxed area represents the inoculation site on the dorsal region of the mouse. Bars 2 mm.

Previous studies addressing the effect of the tissue culture cells on in vitro activity have incubated AMPs with cells prior to adding viruses to the system. Although these types of experiments yield valuable information, they cannot be easily controlled for the multiple variables at play in vivo. A clearer picture of the complex role that cathelicidins play in vivo can be studied by directly examining the effects of cathelicidin deficiency on pox lesion development. $2 \times 10^5$ PFUs of the virus were inoculated by scarification with 15 pricks into the skin of five C57Bl/6, four BALB/c, six 129/SVJ background, and six homozygous CRAMP knock-out (Cnlp$^{-/-}$) mice in the SVJ/129 background. Cnlp$^{-/-}$ mice develop normally and have normal skin morphology just as control littermates, but have increased susceptibility to infection by Group A *Streptococcus*. Four of six homozygous Cnlp$^{-/-}$ animals demonstrated 2 mm pox lesions by day ten, whereas only one (BALB/c) of 15 control animals had a lesion, and this was <1 mm in diameter (p<0.01, Fisher's exact test). When Cnlp$^{-/-}$ animals were compared to SVJ/129 background animals the p value <0.03. This value is conservative since results of only four of the animals were available. A typical pox lesion is displayed in FIG. 5. Since normal mice rarely demonstrate skin lesions using the scarification method and reports of intradermal inoculation of the Wyeth strain into ear pinna of BALB/c yielded minimal lesions or no lesions, the observed inconsistency in appearance of pox lesions in the control animals is not unexpected. The other two Cnlp$^{-/-}$ animals died within two days of inoculation. Histological changes in the livers and lungs were typical of septic shock. Vaccinia virus RNA was present in the lungs and skin using the methods described herein, the only tissues so studied, of each of the expired animals.

The biological activity of all antimicrobial peptides used in these studies was confirmed against *E. coli* ML35p, and the MBC values for each peptide are displayed in Table 2. HBD-2 exhibited the lowest MBC of 0.10 µM and therefore displayed the greatest antimicrobial activity against ML35p. HNP, LL-37, and HBD-1 exhibited MBC values of 8.42, 0.35, and 16.02 µM, respectively. The negative control peptide 8044 did not exhibit antimicrobial activity against ML35p.

TABLE 2

Minimum bactericidal concentrations against *E. coli* ML35p for antimicrobial peptides[a]

| Peptide | Minimum Bactericidal Concentration (µM) |
|---|---|
| HNP | 8.42 ± 0.43 |
| HBD-1 | 16.03 ± 1.20 |
| HBD-2 | 0.10 ± 0.02 |
| LL-37 | 0.35 ± 0.01 |

[a]Control peptide 8044 did not possess antimicrobial activity against ML35p.

Although relatively low concentrations of HNP, HBD-1, and HBD-2 were sufficient to exhibit antibacterial activity against ML35p, concentrations as high as 50 µM did not inhibit vaccinia virus replication. In contrast, a concentration-dependent inhibition (p<0.001) of viral replication was observed in tissue culture cells after infection with a virion preparation, consisting primarily of IMV, that had been pre-incubated with human (LL-37) and murine (CRAMP) cathelicidins. Significant reduction in viral replication by LL-37 and CRAMP was observed with concentrations as low as 25 µM. The control peptide 8044 possessed no antiviral activity against vaccinia virus.

Electron microscopy of virions exposed to LL-37, and defensin HNP-1, and control peptides demonstrated a concentration-dependent effect of only LL-37 on the structure of the IMV, including loss of integrity of the double-layered external envelope as well as that of the internal structure (see, e.g., FIG. 4). In contrast, defensins and control peptides did not have an effect on virion structure. Examination of untreated virions did not identify similar structural changes, thus lessening the possibility that apparent alterations in structure are due to sectioning artifacts. A dose-dependent effect of in vitro incubation of LL-37 on the numbers and percentages of altered virions was found (see Table 1).

Previous studies addressing the effect of the tissue culture cells on in vitro activity have incubated antimicrobial peptides with cells before adding viruses to the system. Although these types of experiments yield valuable information, they cannot easily control for the multiple variables at play in vivo. The physiological role of cathelicidin in vivo can be evaluated using a cathelicidin-deficient murine model and monitoring pox lesion development in inoculated skin. Upon comparison with the 129/SVJ wild-type control, Cnlp$^{-/-}$ mice exhibited significant differences (p<0.03) in lesion size and number.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A purified cationic peptide consisting of a sequence as set forth in SEQ ID NO:3 that has an antiviral activity.

2. A method for inhibiting the spread and/or the risk of infection of a virus infection comprising contacting a virus with an inhibiting effective amount of a cationic antiviral peptide composition, the antiviral peptide consisting of SEQ ID NO:3, wherein the virus is selected from a pox virus, a herpes virus, vaccinia virus, and papilloma virus.

3. The method of claim 2, wherein the contacting is in vitro.

4. The method of claim 3, wherein the contacting is on a surface suspected of having viral particles.

5. The method of claim 2, wherein the contacting is in vivo.

6. The method of claim 5, wherein the contacting in vivo is by topical administration.

7. The purified cationic peptide of claim 1, further comprising a pharmaceutically acceptable carrier.

8. The purified cationic peptide of claim 7, wherein the pharmaceutical acceptable carrier is useful for formulating a lotion, cream, gel, ointment or spray.

9. The pharmaceutical composition of claim 7, wherein the pharmaceutical compositions is for topical administration.

* * * * *

UNITED STATES PATENT AND TRADEMARK OFFICE
CERTIFICATE OF CORRECTION

| | |
|---|---|
| PATENT NO. | : 7,777,000 B2 |
| APPLICATION NO. | : 10/546739 |
| DATED | : August 17, 2010 |
| INVENTOR(S) | : Richard L. Gallo, Donald Y. M. Leung and James F. Jones |

Page 1 of 1

It is certified that error appears in the above-identified patent and that said Letters Patent is hereby corrected as shown below:

Please replace lines 17-19 of column 1 with the following:

--This invention was made with Government Support under Grant Nos. AR41256 and AI052453 awarded by the National Institutes of Health. The U.S. Government has certain rights in this invention.--

Signed and Sealed this

Thirty-first Day of January, 2012

David J. Kappos
*Director of the United States Patent and Trademark Office*